(12) United States Patent
Dacosta et al.

(10) Patent No.: US 11,179,234 B2
(45) Date of Patent: Nov. 23, 2021

(54) LIGAMENT FIXATION SYSTEM, IMPLANTS, DEVICES, AND METHODS OF USE

(71) Applicant: Paragon 28, Inc., Englewood, CO (US)

(72) Inventors: Albert Dacosta, Lone Tree, CO (US); Sean Gill, Denver, CO (US); Peter Andrew Mladinich, Lakewood, CO (US); Richard David Hunt, Arvada, CO (US)

(73) Assignee: Paragon 28, Inc., Englewood, CO (US)

( * ) Notice: Subject to any disclaimer, the term of this patent is extended or adjusted under 35 U.S.C. 154(b) by 159 days.

(21) Appl. No.: 16/134,236

(22) Filed: Sep. 18, 2018

(65) Prior Publication Data

US 2019/0083232 A1 Mar. 21, 2019

Related U.S. Application Data

(63) Continuation of application No. PCT/US2018/051349, filed on Sep. 17, 2018.
(Continued)

(51) Int. Cl.
*A61F 2/08* (2006.01)
*A61B 17/16* (2006.01)
(Continued)

(52) U.S. Cl.
CPC ........ *A61F 2/0811* (2013.01); *A61B 17/1682* (2013.01); *A61B 17/8061* (2013.01);
(Continued)

(58) Field of Classification Search
CPC ..... A61B 17/16; A61B 17/1682; A61B 17/84; A61B 17/68; A61F 2/08; A61F 2/0811
See application file for complete search history.

(56) References Cited

U.S. PATENT DOCUMENTS

| | | | |
|---|---|---|---|
| 3,953,896 A | | 5/1976 | Treace |
| 4,463,753 A | * | 8/1984 | Gustilo ............... A61B 17/863 |
| | | | 411/386 |

(Continued)

FOREIGN PATENT DOCUMENTS

| | | |
|---|---|---|
| CN | 102670291 | 9/2012 |
| CN | 102920498 | 2/2013 |

(Continued)

OTHER PUBLICATIONS

International Search Report and Written Opinion of the International Searching Authority for PCT/US2018/051349, dated Dec. 3, 2018, 7 pages.

(Continued)

*Primary Examiner* — Christopher J Beccia
(74) *Attorney, Agent, or Firm* — Heslin Rothenberg Farley & Mesiti P.C.; Jacquelyn A. Graff, Esq.

(57) ABSTRACT

Implants, devices, systems, and methods for achieving ligament fixation are disclosed. An implant is disclosed that includes a head member, a breakaway portion, and an anchor member. The anchor member may be coupled to the head member by the breakaway portion. The implant may be designed to fail in fatigue at the breakaway portion. The breakaway portion may thereby extend between a first end of the anchor member and a second end of the head member. The breakaway portion may comprise a circumferential groove. The groove may be configured to concentrate stress forces in situ such that a fatigue failure/fracture occurs at the groove. Insertion instruments for inserting an implant for ligament fixation are also disclosed. Methods of using an implant for achieving ligament fixation are also disclosed.

20 Claims, 11 Drawing Sheets

Related U.S. Application Data

(60) Provisional application No. 62/559,047, filed on Sep. 15, 2017.

(51) Int. Cl.
*A61B 17/86* (2006.01)
*A61B 17/92* (2006.01)
*A61B 17/80* (2006.01)
A61B 17/04 (2006.01)
A61F 2/28 (2006.01)
A61B 90/00 (2016.01)

(52) U.S. Cl.
CPC .......... *A61B 17/8625* (2013.01); *A61B 17/92* (2013.01); *A61B 17/864* (2013.01); *A61B 17/8635* (2013.01); *A61B 2017/044* (2013.01); *A61B 2017/0411* (2013.01); *A61B 2090/037* (2016.02); *A61F 2002/0817* (2013.01); *A61F 2002/0858* (2013.01); *A61F 2002/0882* (2013.01); *A61F 2002/2892* (2013.01); *A61F 2210/0004* (2013.01); *A61F 2250/0031* (2013.01); *A61F 2250/0071* (2013.01)

(56) References Cited

U.S. PATENT DOCUMENTS

| | | |
|---|---|---|
| 4,955,910 A | 9/1990 | Bolesky |
| 5,004,474 A | 4/1991 | Fronk et al. |
| 5,061,137 A | 10/1991 | Gourd |
| 5,152,790 A | 10/1992 | Rosenberg et al. |
| 5,507,812 A | 4/1996 | Moore |
| 5,968,045 A | 10/1999 | Frazier |
| 6,187,008 B1 | 2/2001 | Hamman |
| 6,461,373 B2 | 10/2002 | Wyman et al. |
| 6,652,592 B1 | 11/2003 | Grooms et al. |
| 6,921,402 B2 | 7/2005 | Contiliano |
| 7,235,078 B2 | 6/2007 | West, Jr. |
| 7,235,091 B2 | 6/2007 | Thornes |
| 7,608,098 B1 | 10/2009 | Stone et al. |
| 7,625,395 B2 | 12/2009 | Mückter |
| 7,727,278 B2 | 6/2010 | Olsen et al. |
| 7,955,388 B2 | 6/2011 | Jensen et al. |
| 8,439,976 B2 | 5/2013 | Albertorio et al. |
| 8,597,337 B2 | 12/2013 | Champagne |
| 8,696,716 B2 | 4/2014 | Kartalian et al. |
| 8,696,719 B2 | 4/2014 | Lofthouse et al. |
| 8,864,804 B2 | 10/2014 | Champagne et al. |
| 9,089,371 B1 | 7/2015 | Faulhaber |
| 9,138,219 B2 | 9/2015 | Horrell |
| 9,907,576 B2 * | 3/2018 | Mahajan ............ A61B 17/7032 |
| 2002/0143333 A1 | 10/2002 | von Hoffmann et al. |
| 2004/0172032 A1 | 9/2004 | Jackson |
| 2005/0059972 A1 | 3/2005 | Biscup |
| 2007/0162124 A1 | 7/2007 | Whittaker |
| 2007/0218750 A1 | 9/2007 | Corrao et al. |
| 2007/0282342 A1 | 12/2007 | Niederberger |
| 2009/0198287 A1 | 8/2009 | Chiu |
| 2009/0306777 A1 | 12/2009 | Widmer et al. |
| 2011/0040335 A1 | 2/2011 | Stihl et al. |
| 2011/0184471 A1 | 7/2011 | Foley et al. |
| 2012/0123474 A1 | 5/2012 | Zajac et al. |
| 2012/0150237 A1 | 6/2012 | Combrowski |
| 2012/0172936 A1* | 7/2012 | Horrell ............ A61B 17/0401 606/319 |
| 2012/0271416 A1 | 10/2012 | Mackay |
| 2012/0303038 A1 | 11/2012 | Durante |
| 2013/0030480 A1 | 1/2013 | Donate |
| 2013/0184708 A1 | 7/2013 | Robinson et al. |
| 2013/0338722 A1* | 12/2013 | Yalizis ............ A61B 17/8685 606/312 |
| 2014/0025166 A1 | 1/2014 | Bonutti |
| 2014/0121711 A1 | 5/2014 | Worcel |
| 2014/0214095 A1 | 7/2014 | Rosenwasser et al. |
| 2014/0228866 A1 | 8/2014 | Fallin et al. |
| 2014/0236237 A1* | 8/2014 | Mahajan ............ A61B 17/863 606/270 |
| 2014/0243977 A1 | 8/2014 | Tepic et al. |
| 2015/0051601 A1 | 2/2015 | Larsen et al. |
| 2015/0073475 A1 | 3/2015 | Schaller |
| 2015/0081019 A1 | 3/2015 | Whittaker |
| 2016/0045636 A1 | 2/2016 | Rizk et al. |
| 2016/0287302 A1 | 10/2016 | Horrell et al. |
| 2016/0367303 A1 | 12/2016 | Mahajan et al. |
| 2017/0079698 A1 | 3/2017 | Fallin et al. |
| 2017/0258572 A1 | 9/2017 | Gordon |
| 2018/0092681 A1 | 4/2018 | Lutz |
| 2018/0344374 A1 | 12/2018 | Summitt |
| 2019/0083232 A1 | 3/2019 | DaCosta et al. |
| 2019/0336190 A1 | 11/2019 | Allard et al. |
| 2019/0336270 A1 | 11/2019 | Dacosta et al. |

FOREIGN PATENT DOCUMENTS

| | | |
|---|---|---|
| DE | 19943594 | 4/2001 |
| DE | 10015734 | 9/2001 |
| GR | 20090100297 | 12/2010 |
| WO | 2006124987 | 11/2006 |
| WO | 2010121234 | 10/2010 |
| WO | 2013015754 | 1/2013 |
| WO | 2016133938 | 8/2016 |

OTHER PUBLICATIONS

Porucznik, "Screw vs. tightrope fixation for syndesmotic fractures," AAOS NOW, http://www.aaos.org/news/aaosnow/may08/clinical4.asp, 3 pages, May 2008.

Xu et al., "Flexible fixation of syndesmotic diastasis using the assembled bolt-tightrope system," Scandinavian Journal of Trauma, Resuscitation and Emergency Medicine, vol. 21(71), 9 pages, 2013.

"Interventional procedure overview of suture fixation of acute disruption of the distal tibiofibular syndesmosis," National Institute for Health and Care Excellence, www.nice.org.uk, 43 pages, Jul. 2014.

International Preliminary Report on Patentability for International Application No. PCT/US2018/051349, dated Mar. 17, 2020, 5 pages, International Bureau of WIPO.

International Search Report and Written Opinion of the International Searching Authority for PCT/US2020/050438, dated Dec. 10, 2020, 8 pages.

Extended European Search Report issued in European Patent Application No. 18856721.8, dated May 4, 2021, 8 pages.

Partial Supplementary European Search Report issued in European Patent Application No. 18870486.0 dated Jun. 23, 2021, 13 pages.

* cited by examiner

LIGAMENT FIXATION SYSTEM, IMPLANTS, DEVICES, AND METHODS OF USE

CROSS-REFERENCE TO RELATED APPLICATION

This application is a continuation of International PCT Application No. PCT/US2018/051349, filed Sep. 17, 2018, and entitled Ligament Fixation System, Implants, Devices, and Methods of Use, which claims priority to U.S. Provisional Patent Application No. 62/559,047, filed Sep. 15, 2017, and entitled Ligament Fixation System, Implants, Devices, and Methods of Use, which are hereby expressly incorporated herein by reference in their entireties.

TECHNICAL FIELD

The present invention relates generally to general, podiatric, and orthopaedic surgery related to fixation of ligaments. More specifically, but not exclusively, the present invention relates to devices, systems, and methods for achieving ligament fixation.

BACKGROUND OF THE INVENTION

Syndesmotic injuries are a result of trauma (not specific to sports injuries) and can occur as a purely ligamentous injury or in combination with an ankle fracture. These ligaments become disrupted, separated, or injured where semi-constrained approximation and fixation is needed to aide in healing without the need for a second surgery, such as removing a rigid fixation screw. The current standard of care for syndesmotic injuries involves either rigid fixation with a screw, or a tether-based constraint across the entire width of the ankle (TightRope, etc.).

The more rigid screw-based fixation is simple to implant and stabilizes the joint, but fails to allow any motion at all, as would normally exist physiologically. This limits the patient's range of motion, and unpredictable screw failure locations can result in damage to existing bone and patient pain.

Tethered constraints, such as the Arthrex Tightrope, do allow for motion of the joint, but by spanning the entire width of the ankle, fail to mimic the intact ligament structures of the syndesmosis in terms of attachment location and distance between the tibia and fibula. However, tethered constraints result in a necessary decrease in structural strength due to the surgical technique of the Tightrope and like devices involving drilling a hole through both the tibia and fibula which remains unfilled by structural material (e.g. a metal screw).

Thus, new and improved devices, systems, and methods for achieving ligament fixation are needed to overcome the above-noted drawbacks of the currently available solutions for addressing syndesmotic injuries.

SUMMARY OF THE INVENTION

The present disclosure is directed toward devices and methods for use in ligament fixation. The devices, systems, and methods for achieving ligament fixation.

In one aspect of the present disclosure provided herein, is an implant. The implant including a head member and an anchor member coupled to the head member.

In another aspect of the present disclosure provided herein, is a method for inserting an implant. The method including obtaining the implant. The implant including a head member and an anchor member coupled to the head member. The method also including engaging the implant with an insertion instrument and inserting the implant into a patient to position the head member in a first bone and the anchor member in a second bone.

In another aspect, the present disclosure provides an implant comprising a head member, a breakaway portion and an anchor member coupled to the head member. The head member coupling to the anchor member by the breakaway portion.

In some embodiments, the breakaway portion extends between a first end of the anchor member and a second end of the head member. In some embodiments, the breakaway portion comprises a circumferential groove. In some embodiments, the circumferential groove defines a first diameter that is less than a second diameter defined by a portion of the head member positioned proximate to the breakaway portion and a third diameter defined by a portion of the anchor member positioned proximate to the breakaway portion. In some embodiments, a ratio of the first diameter to the second and/or the first diameter to the third diameter is within the range of 64% to 89%.

In some embodiments, the breakaway portion comprises at least one opening extending in a radial direction from a center axis of the breakaway portion. In some embodiments, the breakaway portion comprises openings positioned around a circumference of the breakaway portion. In some embodiments, the breakaway portion comprises at least one through hole extending through the diameter of the implant.

In some embodiments, the head member comprises a shaft portion with a first end and a second end extending from the breakaway portion, a head portion extending from the first end of the shaft member, and a tool engagement opening extending into the head portion toward the second end of the shaft portion. In some embodiments, a portion of the shaft portion comprises external threads. In some embodiments, a portion of the shaft portion at the second end is void of external threads.

In some embodiments, the anchor member comprises a shaft portion with a first end and a second end, a proximal coupling portion extending from the first end of the shaft portion of the anchor member to the breakaway portion, and a distal portion extending from the second end of the shaft portion of the anchor member. In some embodiments, a portion of the shaft portion of the anchor member comprises external threads. In some embodiments, the proximal coupling portion is void of external threads.

In some embodiments, the proximal coupling portion comprises removal members positioned around the circumference of the anchor member. In some embodiments, the removal members comprise outer planar surfaces circumferentially arranged about the proximal coupling portion. In some embodiments, the outer planar surfaces form an external hexagonal drive feature. In some embodiments, the proximal coupling portion comprises an internal drive opening extending into the implant from an end of the distal portion of the anchor member.

In some embodiments, the distal portion comprises a feature positioned around a circumference of the anchor member. In some embodiments, the feature comprises at least one cutting flute. In some embodiments, the feature comprises a plurality of circumferentially arranged longitudinally extending flutes. In some embodiments, the feature comprises outer planar surfaces circumferentially arranged about the anchor member.

In some embodiments, the head member, the breakaway portion and the anchor member are integral. In some embodiments, the implant is of one-piece construction.

In some embodiments, the implant comprises a cannulated opening extending through the entire length of the implant from a proximal head portion of the head member defining a first end of the implant to a distal end of the anchor member defining a second end of the implant.

In some embodiments, the breakaway portion is formed from a bio-resorbable material.

In another aspect, the present disclosure provides a method for inserting an implant comprising obtaining an implant, the implant comprising a head member, a breakaway portion; and an anchor member coupled to the head member, wherein the head member is coupled to the anchor member by the breakaway portion. The method further comprises engaging the head member of the implant with an insertion instrument. The method further comprises inserting the implant into a patient such that the head member is positioned within a first bone, the anchor member is positioned within a second bone, and the breakaway portion is positioned at least partially within a gap extending between the first and second bones.

In some embodiments, the implant comprises an implant described above. In some embodiments, the first bone is a fibula, the second bone is a tibia, and the gap is a tibiofibular space. In some embodiments, the inserting the implant comprises rotating the implant about an axis of rotation thereof while in contact with at least one of the first and second bones.

In another aspect, the present disclosure provides a system that comprises a plurality of implants, an insertion instrument for coupling to the head member of the implant, and a removal instrument for coupling to the anchor member of the implant. The implant may comprise an implant described above.

In some embodiments, the insertion instrument is configured to removable couple with the head member and rotate the implant about an axis of rotation thereof. In some embodiments, the removal instrument is configured to removable couple with the anchor member and rotate the implant about an axis of rotation thereof.

In another aspect, the present disclosure provides a system that comprises a plurality of implants, each implant comprising an implant described above, the lengths of at least one of the head members and the anchor members of the plurality of implants being different.

In some embodiments, the system further comprises an insertion instrument configured to removable couple with the head member and rotate the implant about an axis of rotation thereof. In some embodiments, the system further comprises a removal instrument configured to removable couple with the anchor member and rotate the implant about an axis of rotation thereof.

In another aspect, the present disclosure provides an implant comprising a head member, a breakaway portion and an anchor member coupled to the head member, the head member being coupled to the anchor member by the breakaway portion. In some embodiments, the breakaway portion extends between a first end of the anchor member and a second end of the head member. In some such embodiments, the breakaway portion comprises a circumferential groove that defines a first diameter that is less than a second diameter defined by a portion of the head member positioned proximate to the breakaway portion and a third diameter defined by a portion of the anchor member positioned proximate to the breakaway portion. In some such embodiments, a ratio of the first diameter to the second and/or the first diameter to the third diameter is within the range of 64% to 89%.

In some embodiments, the breakaway portion comprises a plurality of openings positioned around a circumference of the breakaway portion that extend in a radial direction from a center axis of the breakaway portion. In some embodiments, the breakaway portion comprises at least one through hole extending through a diameter of the breakaway portion.

In some embodiments, the head member comprises a shaft portion with a first end and a second end extending from the breakaway portion, a head portion extending from the first end of the shaft member, and a tool engagement opening extending into the head portion toward the second end of the shaft portion. In some such embodiments, the shaft portion comprises external threads, and wherein a portion of the shaft portion at the second end is void of external threads.

In some embodiments, the anchor member comprises a shaft portion with a first end and a second end, a proximal coupling portion extending from the first end of the shaft portion of the anchor member to the breakaway portion, and a distal portion extending from the second end of the shaft portion of the anchor member. In some such embodiments, at least a portion of the shaft portion of the anchor member comprises external threads, and wherein the proximal coupling portion is void of external threads. In some other such embodiments, the proximal coupling portion comprises outer planar surfaces circumferentially arranged about the proximal coupling portion. In some other such embodiments, the proximal coupling portion comprises an internal drive opening extending into the implant from an end of the distal portion of the anchor member. In some other such embodiments, the distal portion comprises at least one cutting flute. In some other such embodiments, the distal portion comprises a plurality of circumferentially arranged longitudinally extending flutes.

In some embodiments, the head member, the breakaway portion and the anchor member are integral. In some embodiments, the implant comprises a cannulated opening extending through an entire length of the implant extending from a proximal head portion of the head member defining a first end of the implant to a distal end of the anchor member defining a second end of the implant. In some embodiments, the breakaway portion is formed of a bio-resorbable material.

In another aspect, the present disclosure provides a method for inserting an implant comprising obtaining an implant. The implant comprises a head member, a breakaway portion and an anchor member coupled to the head member, the head member being coupled to the anchor member by the breakaway portion. The method further comprises engaging the head member of the implant with an insertion instrument, and inserting the implant into a patient such that the head member is positioned within a first bone, the anchor member is positioned within a second bone, and the breakaway portion is positioned at least partially within a gap extending between the first and second bones.

In some embodiments, the first bone is a fibula, the second bone is a tibia, and the gap is a tibiofibular space. In some embodiments, the breakaway portion comprises a circumferential groove that defines a first diameter that is less than a second diameter defined by a portion of the head member positioned proximate to the breakaway portion and a third diameter defined by a portion of the anchor member positioned proximate to the breakaway portion, and a ratio of the first diameter to the second and/or the first diameter to the third diameter is within the range of 64% to 89%. In some such embodiments, the anchor member comprises a distal end portion comprising a plurality of circumferentially arranged longitudally extending flutes.

These and other objects, features and advantages of this invention will become apparent from the following detailed description of the various aspects of the invention taken in conjunction with the accompanying drawings.

BRIEF DESCRIPTION OF THE DRAWINGS

The accompanying drawings, which are incorporated in and constitute a part of the specification, illustrate embodiments of the invention and together with the detailed description herein, serve to explain the principles of the invention. It is emphasized that, in accordance with the standard practice in the industry, various features are not drawn to scale. In fact, the dimensions of the various features may be arbitrarily increased or reduced for clarity of discussion. The drawings are only for purposes of illustrating preferred embodiments and are not to be construed as limiting the invention.

DETAILED DESCRIPTION FOR CARRYING OUT THE INVENTION

Figure 1:
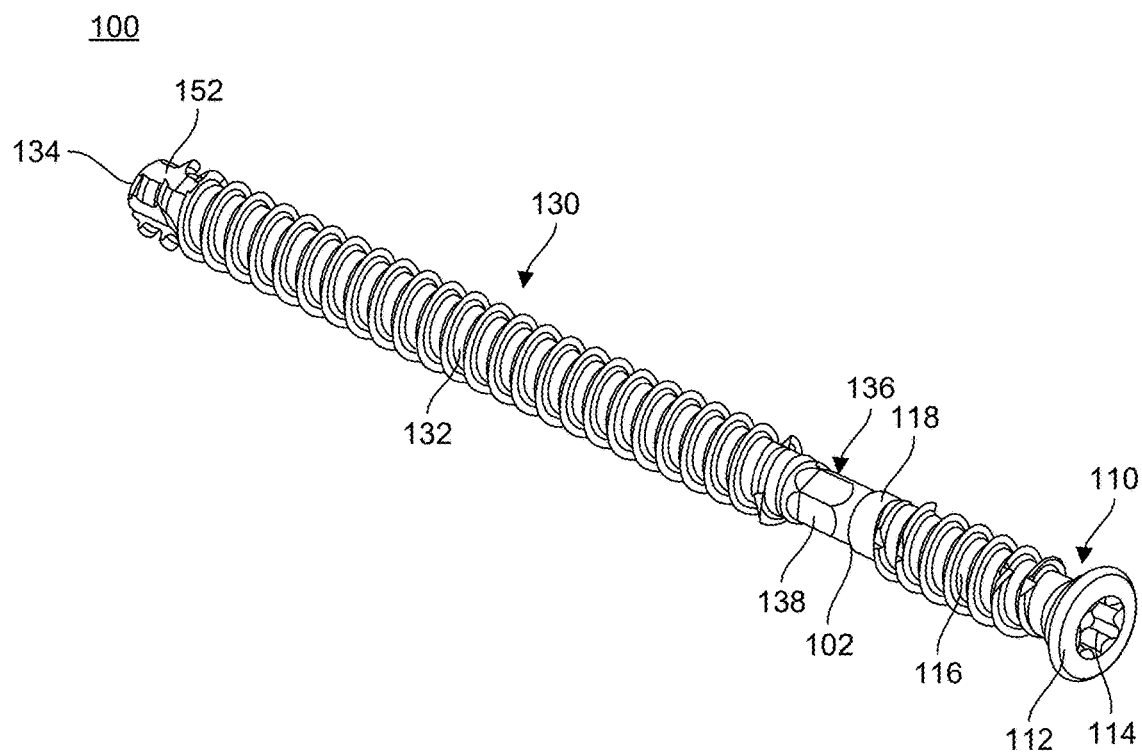
FIG. 1 is a side perspective view of one embodiment of an implant, in accordance with an aspect of the present disclosure.

Generally stated, disclosed herein are devices and systems for achieving ligament fixation. Further, methods for using the devices and systems to achieve ligament fixation are discussed.

In this detailed description and the following claims, the words proximal, distal, anterior or plantar, posterior or dorsal, medial, lateral, superior and inferior are defined by their standard usage for indicating a particular part or portion of a bone or implant according to the relative disposition of the natural bone or directional terms of reference. For example, "proximal" means the portion of a device or implant nearest the torso, while "distal" indicates the portion of the device or implant farthest from the torso. As for directional terms, "anterior" is a direction towards the front side of the body, "posterior" means a direction towards the back side of the body, "medial" means towards the midline of the body, "lateral" is a direction towards the sides or away from the midline of the body, "superior" means a direction above and "inferior" means a direction below another object or structure. Further, specifically in regards to the foot, the term "dorsal" refers to the top of the foot and the term "plantar" refers the bottom of the foot.

Similarly, positions or directions may be used herein with reference to anatomical structures or surfaces. For example, as the current implants, devices, instrumentation and methods are described herein with reference to use with the bones of the ankle, the bones of the foot, ankle and lower leg may be used to describe the surfaces, positions, directions or orientations of the implants, devices, instrumentation and methods. Further, the implants, devices, instrumentation and methods, and the aspects, components, features and the like thereof, disclosed herein are described with respect to one side of the body for brevity purposes. However, as the human body is relatively symmetrical or mirrored about a line of symmetry (midline), it is hereby expressly contemplated that the implants, devices, instrumentation and methods, and the aspects, components, features and the like thereof, described and/or illustrated herein may be changed, varied, modified, reconfigured or otherwise altered for use or association with another side of the body for a same or similar purpose without departing from the spirit and scope of the invention. For example, the implants, devices, instrumentation and methods, and the aspects, components, features and the like thereof, described herein with respect to the right leg may be mirrored so that they likewise function with the left leg. Further, the implants, devices, instrumentation and methods, and the aspects, components, features and the like thereof, disclosed herein are described with respect to the leg for brevity purposes, but it should be understood that the implants, devices, instrumentation and methods may be used with other bones of the body having similar structures.

Referring to the drawings, wherein like reference numerals are used to indicate like or analogous components throughout the several views, and with particular reference to FIGS. 1-23, there is illustrated implants 100, 200 and 300. The implants 100, 200 and 300 may be, for example, supportive enough to heal syndesmotic ligaments post-operatively. The implants 100, 200 and 300 may also, for example, selectively constrain motion in all directions to allow for the ligaments to heal. After the syndesmotic ligaments heal, the implants 100, 200 and 300 allow for physiologic motion. The components of the implants 100, 200 and 300 may be made of, for example, titanium, stainless steel, polymers, and resorbable or time release materials.

The implants 100, 200 and 300 also allow for screw-like implantation and temporary rigid fixation, then, after insertion, the implants 100, 200 and 300 are designed to break away (e.g., fracture and/or dissolve) at a specific location after a plurality of loading cycles (e.g., a number of loading cycles that may differ according to load). The loading cycles may be a plurality of non-weight bearing and/or weight bearing loading cycles. The implants 100, 200 and 300 may be designed to fail (i.e., fracture or break) in fatigue at the breakaway portion. In some embodiments, the implants 100, 200 and 300 may be designed to concentrate forces that are applied to the implants 100, 200 and 300 (e.g., after implantation/in situ) at/to the breakaway portion such that failure (e.g., fatigue fracture) occurs at the at the breakaway portion. In some embodiments, the breakaway portion may comprise a circumferential groove. The temporary rigid fixation of the implants 100, 200 and 300 gives the fixed joint time to stabilize through healing and then allows physiologic motion after breakaway (e.g., fracture and/or dissolve) of the breakaway portion. The breakaway location is set in the space or gap between the fibula and tibia, where the subsequent risk of damage to native bone is lower. In this way, forces and/or stress applied to the implants 100, 200 and 300 after implantation may be concentrated to the breakaway portion, which may be configured to fail (e.g., fracture) due to cyclic loading (i.e., fail in fatigue). The surgical method includes drilling a hole through both the tibia and fibula and then inserting an implant 100, 200 and 300 to fill the bone cavities to provide a stronger post-op construct.

Figure 2:
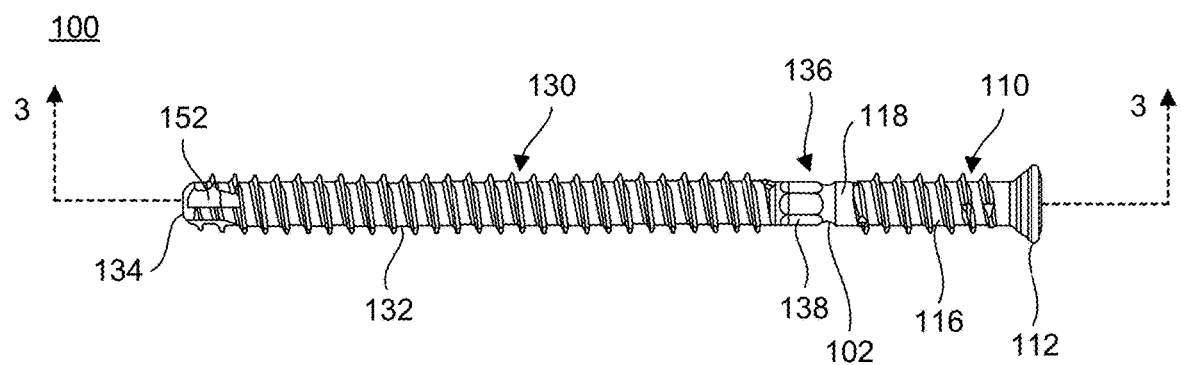
FIG. 2 is a side view of the implant of FIG. 1, in accordance with an aspect of the present disclosure.
Figure 3:
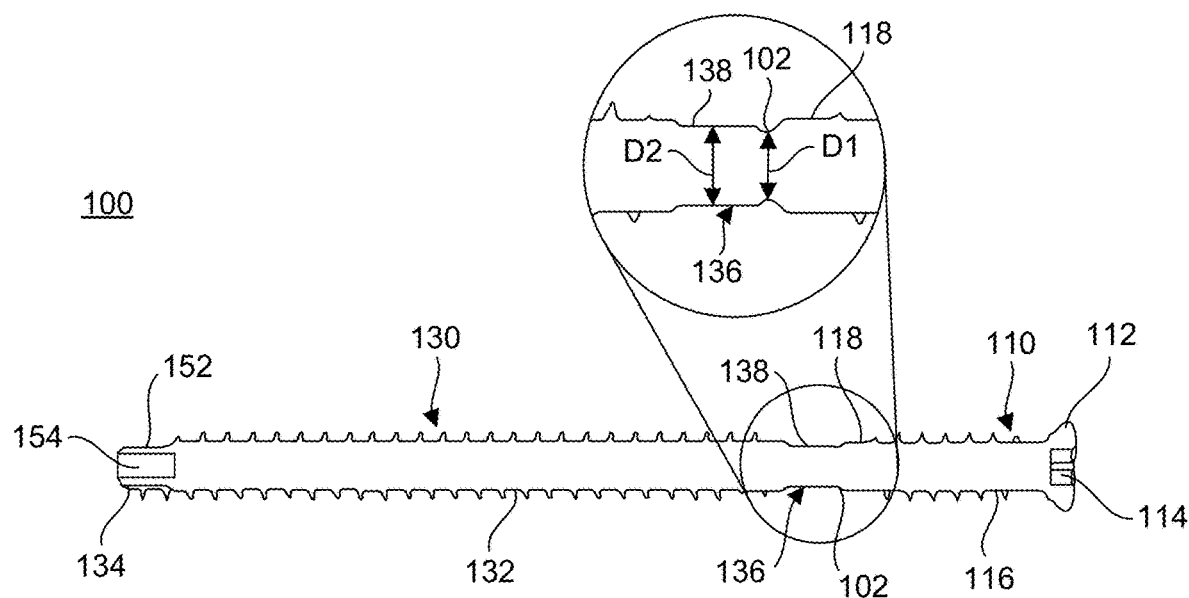
FIG. 3 is a first cross-sectional view of the implant of FIG. 1 taken along line 3-3 in FIG. 2, in accordance with an aspect of the present disclosure.

Referring now to FIGS. 1-12, the implant 100 is illustrated. The implant 100 includes a head member or fibula member 110, an anchor member or tibia member 130, and a breakaway portion or notch 102 positioned between the head member 110 and the anchor member 130. The head member 110 is coupled to the anchor member 130 by the breakaway portion 102. The breakaway portion 102 may be recessed into the exterior surface of the implant 100 to form a notch, groove, recess, necking or the like, as shown in FIGS. 1-3. The implant 100 may be, for example, a solid or one-piece construct, as shown in FIG. 3. It is also contemplated that the implant 100 may optionally include, for example, a cannulated opening or through hole (not shown) which extends the entire length of the implant 100. The implant 100 may have a length of, for example, approximately 40 mm to 70 mm. In an embodiment, the length of the head member 110 may remain constant and the length of the anchor member 130 may be variable to correspond to the varying size of a patient's bones 180, 182. Alternatively, in another embodiment, the head member 110 may, for example, be available in multiple lengths to correspond to the varying size of a patient's bones 180, 182 and the length of the anchor member 130 may remain constant. In yet another embodiment, both the head member 110 and the anchor member 130 may be available in multiple lengths to allow for selection based on the size of the patient's bones 180, 182. The head member 110 may have a length of, for example, between approximately 10 mm and 20 mm. The anchor member 130 may have a length of, for example, between approximately 20 mm and 60 mm.

With continued reference to FIGS. 1-3, the head member or fibula member 110 may include a head or button portion 112 at a first end of the implant 100 and a shaft member or threaded portion 116 extending from the head 112. The head 112 may also include a tool engagement opening 114 positioned on a surface that is opposite the shaft member 116, as shown in FIGS. 1 and 3. The tool engagement opening 114 may have a non-circular or multi-lobed shape, although other polygonal shapes are also contemplated, including a hexagonal shape or a hexalobular drive feature. The head member 110 may also include a distal coupling portion 118 at a second end of the shaft member 116 opposite the head 112. The distal coupling portion 118 is connected to the breakaway notch 102 on a first side. The distal coupling portion 118 may be, for example, a portion of the shaft member 116 which is smooth or lacks threads. The implant 100 may be made of, for example, titanium, stainless steel, polymer, or another like material as known by one of ordinary skill in the art.

Figure 4:
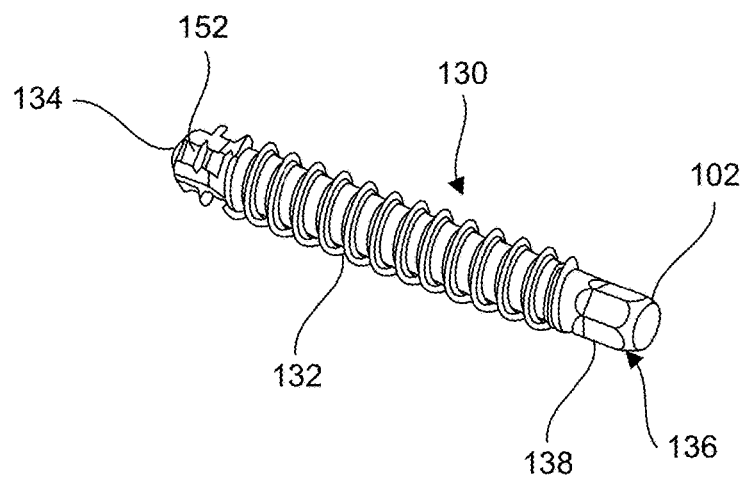
FIG. 4 is a side perspective view of the breakaway portion of the anchor member of the implant of FIG. 1, in accordance with an aspect of the present disclosure.

The anchor member or tibia member 130 may include a shaft portion or threaded portion 132, as shown in FIGS. 1-4. The shaft portion 132 may include a distal end 134 at the second end of the implant 100 and the shaft portion 132. The shaft portion 132 may also include a proximal coupling portion 136 at a first end of the shaft portion 132 opposite the distal end 134. The proximal coupling portion 136 is connected to the breakaway portion 102 on a second side opposite the distal coupling portion 118 of the head member 110. The proximal coupling portion 136 may be, for example, a section of the shaft portion 132 which lacks threads and includes at least one lateral removal member 138. The at least one lateral removal member 138 may be, for example, an external hexagonal drive feature, as shown in FIGS. 1-7. As shown in FIGS. 1-4, 11 and 12, the anchor member 130 may also include a distal feature or portion 152 positioned at the distal or second end 134 of the anchor member 130 adjacent to the distal end 134. The distal portion 152 may include surfaces for engaging an extraction instrument (not shown). The surfaces of the distal portion 152 may form, for example, a hexagonal drive portion similar to the at least one lateral removal member 138. The distal portion 152 may further be, for example, a plurality of circumferentially spaced or arranged longitudinally extending flutes (e.g., cutting flutes) or teeth, as shown in FIGS. 1 and 2. For example, as shown in FIGS. 1, 2 and 4, the distal feature or portion 152 may comprise four (4) circumferentially spaced or arranged longitudinally extending flutes or indentations. The distal end 134 of the anchor member 130 may also include, for example, an opening or recess 154 extending into the core of the anchor member 130 along the longitudinal axis of the implant 100, as shown in FIG. 3. In an embodiment of the anchor member 130 including a cannulation (not shown), the opening 154 may be, for example, continuous or aligned with the cannulation.

As shown in FIGS. 1-4, the breakaway portion 102 may be, for example, a notch, groove, necking, or recess into the exterior surface of the implant 100. The notch, groove, necking, or recess may have, for example, a curved, rounded, or "V" shape. Alternatively, the breakaway portion 102 may be, for example, a resorbable material or member positioned between and coupling the head member 110 to the anchor member 130. The resorbable breakaway portion 102 may include, for example, a notch, groove, necking, or recess with a curved, rounded or "V" shape or, alternatively, the resorbable breakaway portion 102 may be flush with the exterior surface of the distal coupling portion 118 and proximal coupling portion 136. The resorbable breakaway portion 102 may initially provide a connection between the head member 110 and anchor member 130 to constrain motion between the bones 180, 182. Then, once the resorbable breakaway portion 102 breaks down and resorbs into the patient, the head member 110 and anchor member 130 will be separated and motion between the bones 180, 182 will no longer be constrained. When the implant 100 with the breakaway portion 102 breaks, the proximal end of the anchor member 130 may be, for example, smooth or flat. The implant 100 may have, for example, a breakaway feature ratio between the circumferential breakaway notch or groove of the breakaway portion 102 and the proximate portion of the distal coupling portion 118 and/or the proximal coupling portion 136, such as a breakaway feature ratio within the range of 64% to 89%, and more preferably within the range of 75% to 82%. For example, as shown in FIG. 3, the ratio of the (maximum) diameter D1 of the circumferential breakaway notch or groove of the breakaway portion 102 to the (maximum) diameter D2 of the proximate portion of the distal coupling portion 118 D2 and/or the proximal coupling portion 136 (i.e., D1/D2) may be within the range of 64% to 89%, and more preferably within the range of 75% to 82%. As noted above, the implant 100 may be configured such that the stress applied to the implant 100 in situ is concentrated at/to the breakaway portion 102 (e.g., the circumferential groove thereof), and the breakaway portion 102 (e.g., the circumferential groove thereof) may be configured to fail (i.e., fracture) in fatigue due to such stresses. The circumferential groove of the breakaway portion 102 may thereby define a (maximum) diameter D1 that is less than a (maximum) diameter D2 defined by a portion of the head member 130 positioned proximate to the breakaway portion 102 (e.g., the distal coupling portion 118) and/or a diameter defined by a portion of the anchor member 130 positioned proximate to the breakaway portion 102 (e.g., the proximal coupling portion 136), as shown in FIG. 3.

Figure 5:
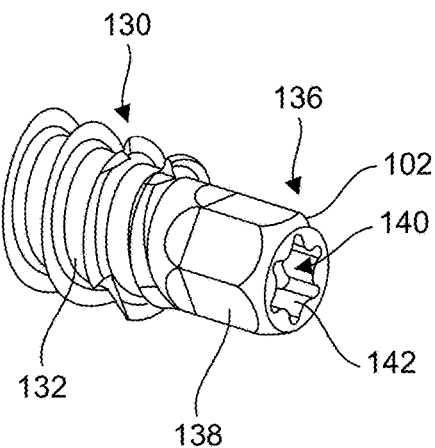
FIG. 5 is a side perspective view of a portion of another breakaway portion of the anchor member of the implant of FIG. 1, in accordance with an aspect of the present disclosure.
Figure 6:
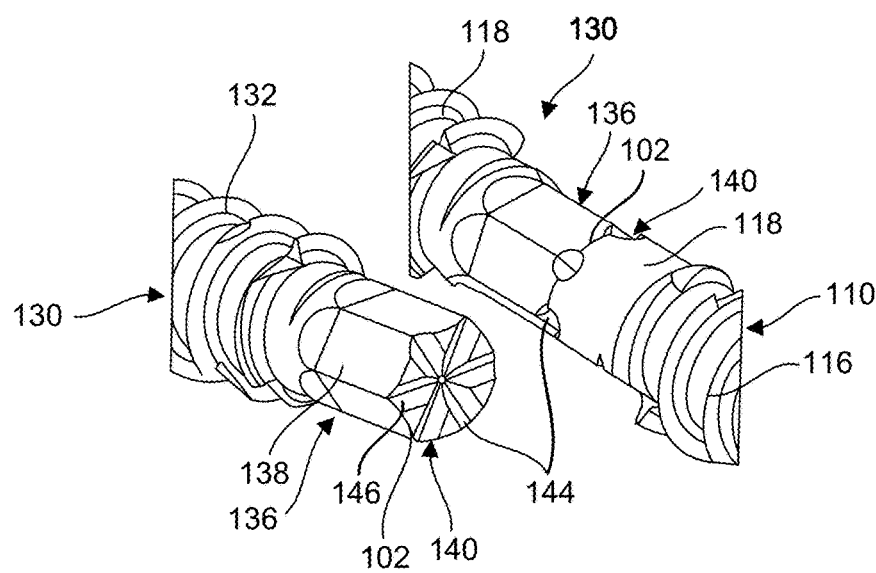
FIG. 6 is a side perspective view of a portion of the implant of FIG. 1 with another breakaway portion of the anchor member with an enlarged view of the end of the anchor member, in accordance with an aspect of the present disclosure.
Figure 7:
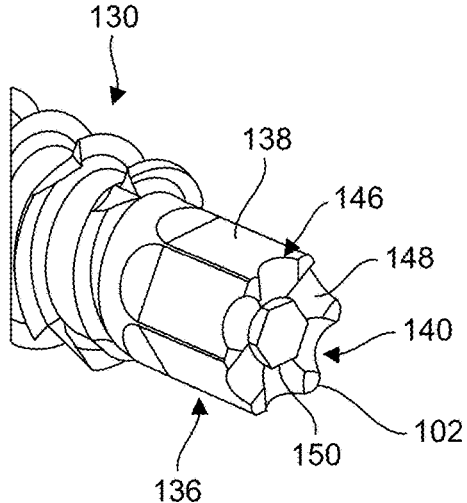
FIG. 7 is a side perspective view of a portion of another anchor member of the implant of FIG. 1, in accordance with an aspect of the present disclosure.

As shown in FIG. 5, the breakaway portion 102 may include, for example, an internal drive feature 140 for receiving an extraction instrument to remove the anchor member 130. The internal drive feature 140 may be, for example, a hexagonal or other multi-lobed drive opening 142. As shown in FIG. 6, the breakaway portion 102 may also include, for example, at least one hole 144. The at least one hole 144 may be, for example, at least one through hole extending through the entire diameter of the implant 100 perpendicular to the longitudinal axis or alternatively, only through a portion of the implant 100. The holes 144 may be radially positioned, for example, between the distal coupling portion 118 of the head member 110 and the proximal coupling portion 136 of the anchor member 130. As shown in FIG. 7, the breakaway portion 102 may include, for example, at least one channel 146 extending into the implant 100 from an exterior surface to form at least one blind hole, pocket or opening 148. In addition, the breakaway portion 102 of FIG. 7 may include an opening 150 positioned, for example, in the center of the anchor member 130 and extend into the anchor member 130 along the longitudinal axis of the implant 100. The breakaway portion 102 is designed or configured to fail at the precise location of the breakaway portion 102. Specifically, the materials and sizes of the implant 100 are selected to withstand a desired torsional force, bending moment, etc. at the breakaway portion 102. Alternative external and internal removal features that allow for engagement of an extraction instrument to remove the anchor member 130 from a lateral side of the patient are also contemplated.

Figure 8:
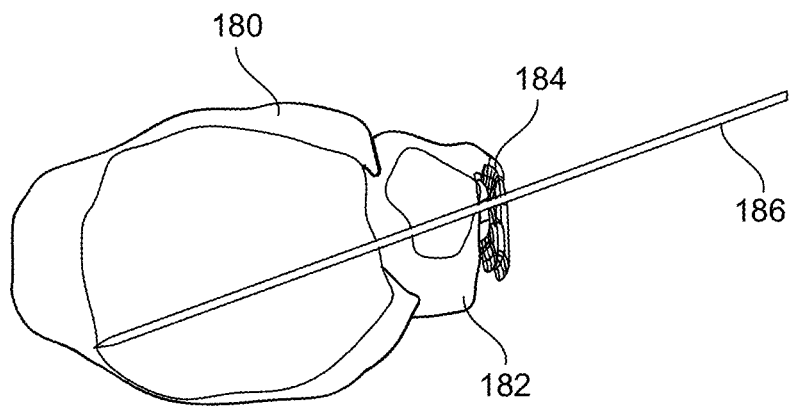
FIG. 8 is a distal, transverse planar view of a fibula and tibia with a k-wire inserted through a plate, the fibula and into the tibia, in accordance with an aspect of the present disclosure.
Figure 9:
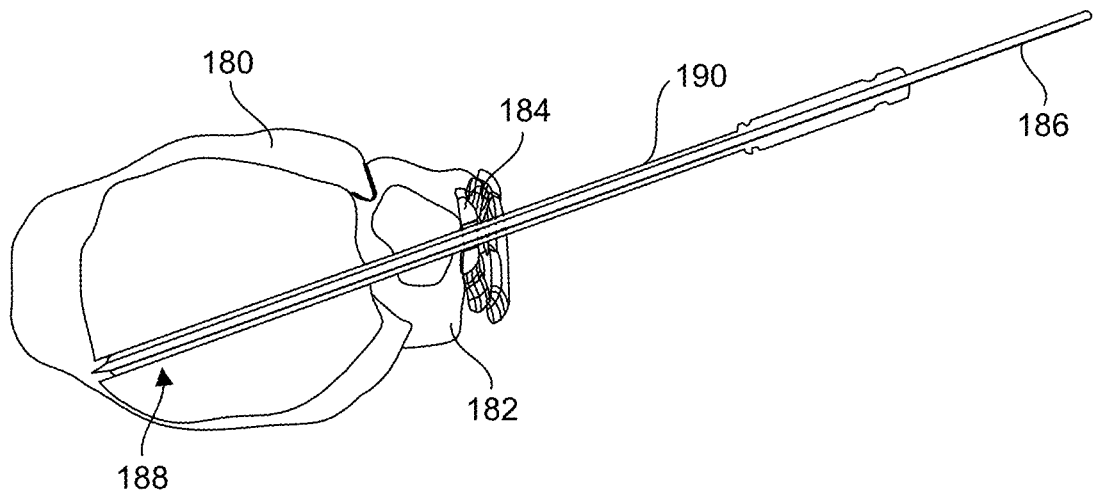
FIG. 9 is a distal, transverse planar view of the bones of FIG. 8 with a cannulated drill inserted over the k-wire of FIG. 8 through the plate, fibula and into the tibia, in accordance with an aspect of the present disclosure.
Figure 10:
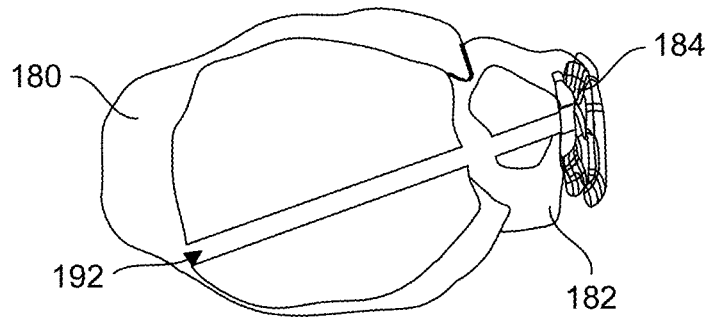
FIG. 10 is a distal, transverse planar view of the bones of FIG. 9 after the drill and k-wire are removed, in accordance with an aspect of the present disclosure.
Figures 11, 12:
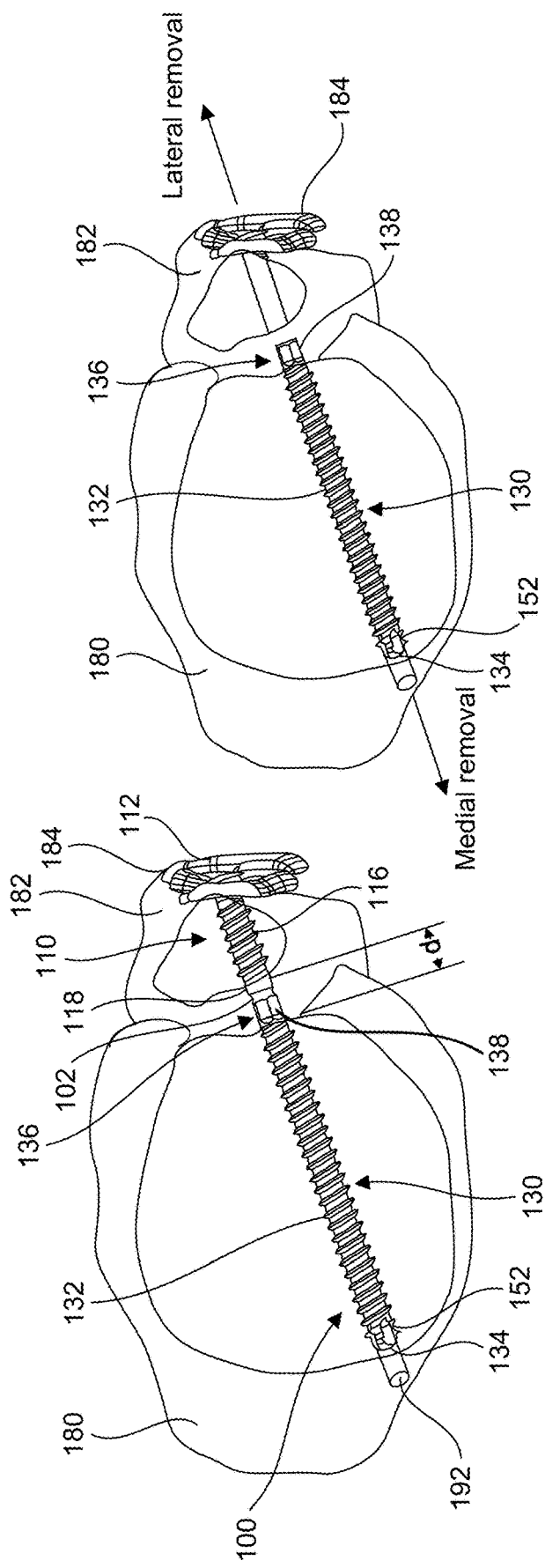
FIG. 11 is a distal, transverse planar view of the bones of FIG. 10 with the implant of FIG. 1 inserted into the drilled opening, in accordance with an aspect of the present disclosure.
FIG. 12 is a distal, transverse planar view of the bones of FIG. 11 with the implant of FIG. 1 after the implant breaks and the head member is removed from the fibula, in accordance with an aspect of the present disclosure.

Referring now to FIGS. 8-12, a method of inserting the implant 100 is shown. The method may include positioning a plate 184 on a bone 182, for example, a fibula, and driving a k-wire or guide wire 186 through two bones 180, 182, for example, a fibula 182 and tibia 180, as shown in FIG. 8. Next, as shown in FIG. 9, a drill 188 may be inserted over the k-wire 186 by aligning a cannulated opening 190 in the drill 188 with the k-wire 186. The drill 188 may be used to drill an opening 192 through the bones 180, 182. The opening 192 may have a diameter, for example, that corresponds to the minor diameter or shaft of the anchor member 130. After the opening 192 is drilled, the drill 188 and k-wire 186 may be removed from the bones 180, 182, as shown in FIG. 10. Optionally, after removing the drill 188 and prior to removing the k-wire 186, measurements of the opening 192 may be taken using a cannulated depth gauge (not shown) inserted over the k-wire 186. Once the measurements are taken the k-wire 186 may then be removed. Alternatively, the k-wire 186 may be removed from the bones 180, 182 and a standard depth gauge (not shown) may be used to take the measurements. For example, an overall or first measurement of the opening or drill hole 192, such as a measurement to the far cortex of the tibia, may be taken using a cannulated depth gauge, standard depth gauge or other like instrument. The surgeon may also take a second measurement of the portion of the opening 192 in the fibula using, for example, a standard depth gauge or like instrument, to determine the size of the head member 110. Then, a driver instrument (not shown) may be used to insert the implant 100 into the opening 192 in the bones 180, 182, as shown in FIG. 11. The implant 100 may be inserted to position the anchor member 130 in the tibia 180, the head member 110 in the fibula 182, and the breakaway notch 102 in a tibiofibular space or gap d, as shown in FIG. 11. The space or gap d may be, for example, approximately 3 mm. The torsional force applied to the head member 110 for inserting the implant 100 may be transmitted to the anchor member 130 through the breakaway portion 102. Next, the driver instrument (not shown) may be removed from head member 110 of the implant 100, as shown in FIG. 11, and the surgical procedure may be completed.

After inserting the implant 100, the breakaway portion 102 will eventually fail or fracture leaving the head member 110 separated from the anchor member 130 and the motion between the tibia 180 and fibula 182 no longer constrained. Once the breakaway portion 102 fails the patient's physiologic motion is restored. Absent any further complications, the head member 110 and anchor member 130 may remain in the patient's fibula 182 and tibia 180, respectively. However, if hardware removal is required, the head member 110 may be removed from the fibula 182 after the breakaway portion 102 fractures, as shown in FIG. 12. In addition, if necessary, the anchor member 130 may be removed from the tibia 180, as well. The anchor member 130 may be removed, for example, medially using the distal drive feature 152 or laterally using the lateral removal member 138 of the proximal coupling portion 136.

FIGS. 13-19 illustrates another exemplary alternative implant 200. The exemplary implant 200 of FIGS. 13-19 is substantially similar to the exemplary implant 100 described above with respect to FIGS. 1-12, and therefore like reference numerals preceded by the numeral "2," as opposed to "1," are used to indicate like elements, aspects, functions, actions, configurations and the like. The implant 200 of FIGS. 13-19 may include any of the elements, aspects, functions, actions, configurations and the like of the implant 100 of FIGS. 1-12. The description above directed thereto with respect to the implant 100 of FIGS. 1-12 thereby equally applies to the exemplary implant 200 of FIGS. 13-19, including description regarding alternative embodiments thereto (i.e., modifications, variations or the like).

As shown in FIGS. 13-19, the implant 200 includes a head member 210, an anchor member 230, and a breakaway portion or notch 204 positioned between the head member 210 and the anchor member 230. The head member 210 is coupled to the anchor member 230 by the intermediate breakaway portion 204. The breakaway portion 204 may include, for example, a notch, recess, necking, or groove with a curved, rounded or "V" shape, which may be recessed into the exterior surface of the implant 200, as shown in FIGS. 13-16. Alternatively, the breakaway portion 204 may be, for example, a resorbable material or member positioned between and coupling the head member 210 to the anchor member 230. The implant 200 with the resorbable material or member may be, for example, integral with the head member 210 and anchor member 230 forming a one-piece construct or, alternatively, may be a three-piece construct coupled together to form the implant 200. The resorbable breakaway portion 204 may include, for example, a notch, groove, necking, or recess with a curved, rounded or "V" shape or, alternatively, the resorbable breakaway portion 204 may be flush with the exterior surface of the distal coupling portion 218 and proximal coupling portion 236. The resorbable breakaway portion 204 may initially provide a fixed connection between the head member 210 and anchor member 230 to constrain motion between the bones 180, 182. Once the resorbable breakaway portion 204 is resorbed into the patient, the head member 210 and anchor member 230 will be separated and motion between the bones 180, 182 will no longer be constrained.

Figure 15:
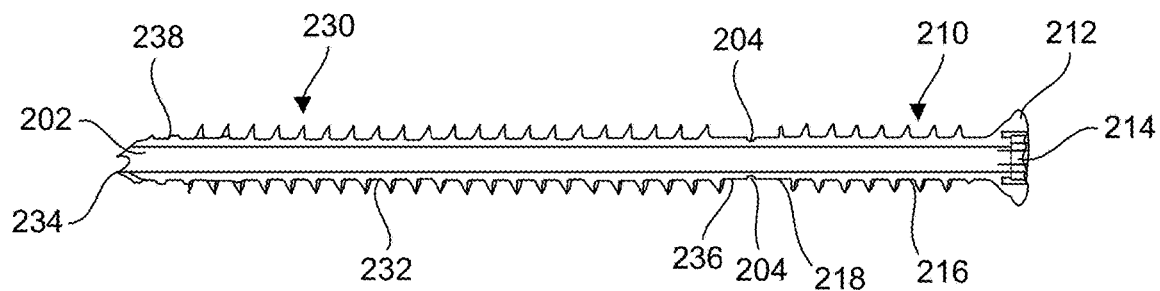
FIG. 15 is a first cross-sectional view of the implant of FIG. 13 taken along line 15-15 in FIG. 14, in accordance with an aspect of the present disclosure.
Figure 16:
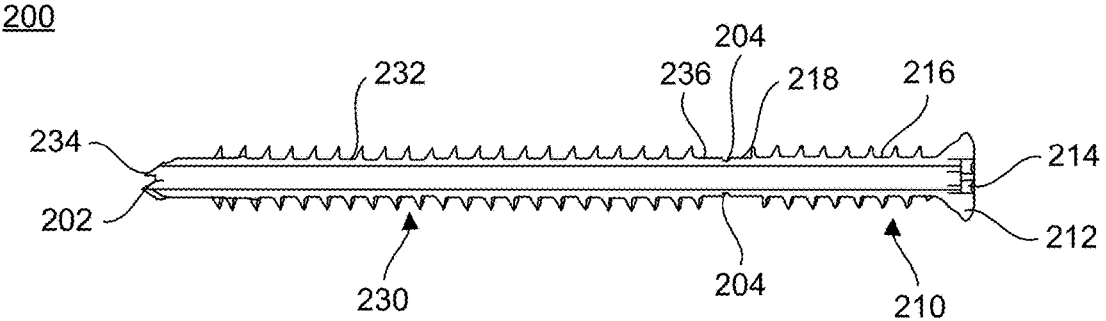
FIG. 16 is a second cross-sectional view of the implant of FIG. 13 taken along a longitudinal line perpendicular to line 15-15 in FIG. 14, in accordance with an aspect of the present disclosure.

The one piece implant 200 may also include, for example, a cannulated opening or through hole 202 extending the entire length of the implant 200, as shown in FIGS. 15 and 16. It is also contemplated that the implant 200 may be, for example a solid implant without a central opening or an implant with a central opening that only extends along a portion of the length of the implant. The implant 200 may be, for example, approximately 40 mm to 70 mm long. In one embodiment, the length of the head member 210 may remain constant with the length of the anchor member 230 being available in multiple sizes to correspond to the varying sizes of a patient's bones 180, 182. Alternatively, in another embodiment, the head member 210 may, for example, be available in multiple lengths to correspond to the varying sizes of a patient's bones 180, 182 with the corresponding length of the anchor member 230 remaining constant. In yet another embodiment, both the head member 210 and the anchor member 230 may be available in multiple lengths to allow for implant matching based on the size of the patient's bones 180, 182. The head member 210 may have a length of, for example, between approximately 10 mm and 20 mm. The anchor member 230 may have a length of, for example, between approximately 20 mm and 60 mm.

Figure 13:
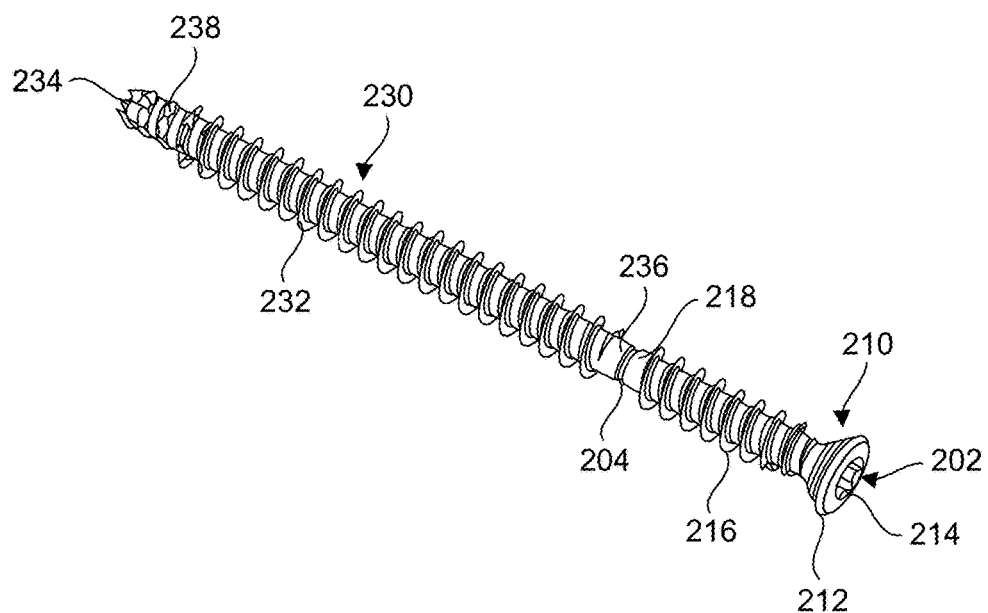
FIG. 13 is perspective side view of another implant, in accordance with an aspect of the present disclosure.
Figure 14:
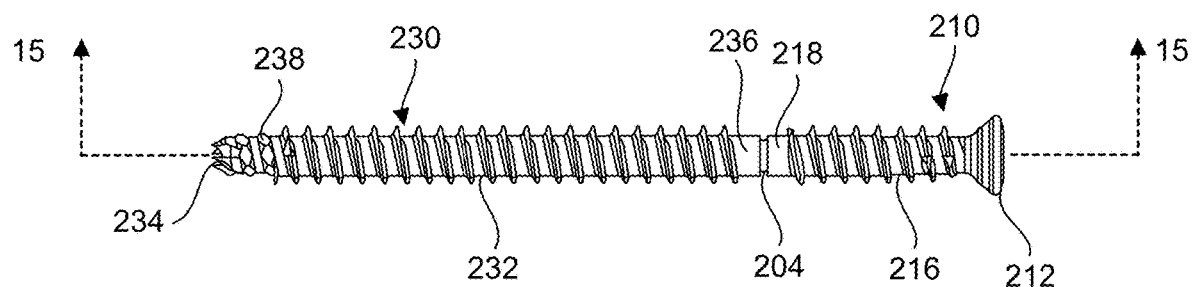
FIG. 14 is a side view of the implant of FIG. 13, in accordance with an aspect of the present disclosure.

With continued reference to FIGS. 12-15, the head member or fibula member 210 may include a head or button portion 212 at a first end of the implant 200 and a shaft member or threaded portion 216 extending from the head 212. The head 212 may also include a tool engagement opening 214 positioned on a surface that is opposite the shaft member 216, as shown in FIGS. 13, 15 and 16. The tool engagement opening 214 may have a multi-lobed shape, although other polygonal shapes are also contemplated, including a hexagonal shape or a hexalobular drive feature. The head member 210 may also include a distal coupling portion 218 at a second end of the shaft member 216 opposite the head 212. The distal coupling portion 218 is connected to the breakaway portion 204 on a first side. The distal coupling portion 218 may be, for example, a portion of the shaft member 216 which is smooth or lacks threads. The cannulated opening 202 may extend through the head member 210 from the tool engagement opening 214 to the distal coupling portion 218. The implant 200 may be made of, for example, titanium, stainless steel, polymer, or another like material as known by one of ordinary skill in the art.

The anchor member or tibia member 230 may include a shaft portion or threaded portion 232, as shown in FIGS. 12-15. The shaft portion 232 may include cutting end 234 at the second end of the implant 200 and the shaft portion 232. The cutting end 234 may include, for example, cutting flutes, teeth or the like. The shaft portion 232 may also include a proximal coupling portion 236 at a first end of the shaft portion 232 opposite the cutting end 234. The proximal coupling portion 236 is connected to the breakaway portion 204 on a second side opposite the distal coupling portion 218 of the head member 210. The proximal coupling portion 236 may be, for example, a section of the shaft portion 232 which is smooth or lacks threads. The cannulated opening 202 may extend through the anchor member 230 from the proximal coupling portion 236 to the cutting end 234. As shown in FIGS. 13-15 and 19, the anchor member 230 may also include a distal feature or portion 238 positioned at the second end of the anchor member 130 adjacent to the cutting end 234. The distal feature 238 may be, for example, a hexagonal drive feature.

Figure 17:
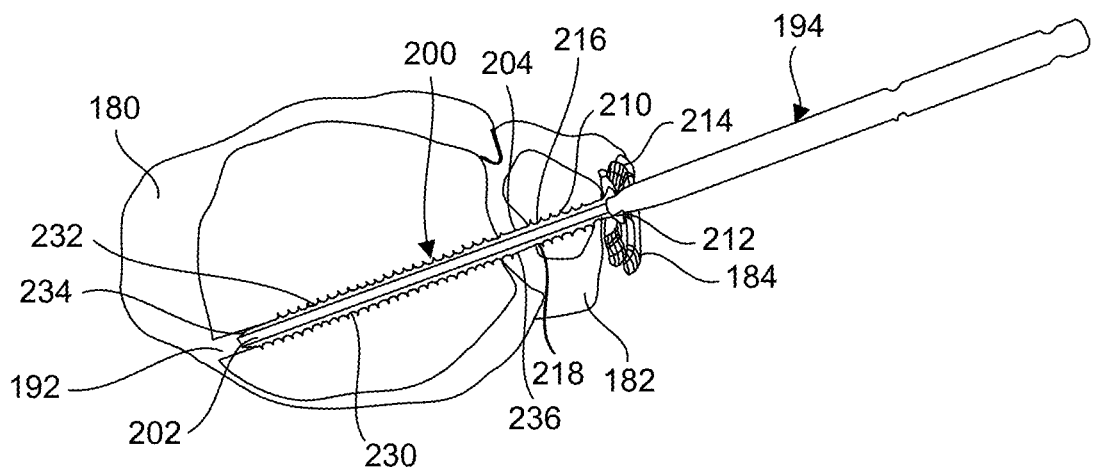
FIG. 17 is a distal, transverse planar view of the bones of FIG. 8 with the implant of FIG. 13 inserted into the drilled opening with a driver instrument, in accordance with an aspect of the present disclosure.
Figure 18:
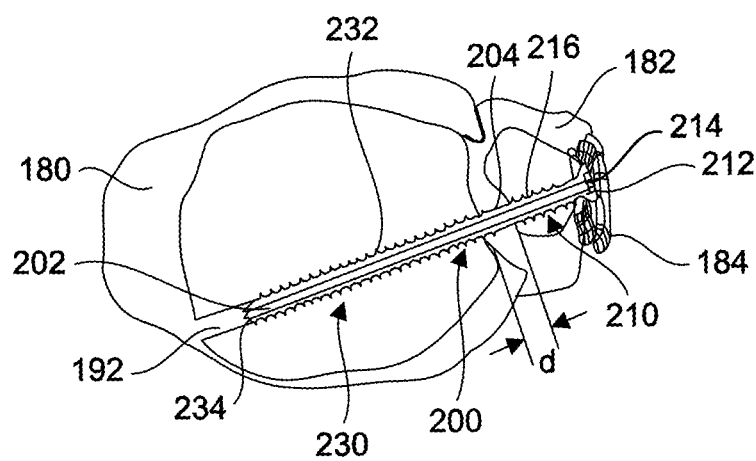
FIG. 18 is a distal, transverse planar view of the bones of FIG. 17 after removal of the driver instrument, in accordance with an aspect of the present disclosure.
Figure 19:
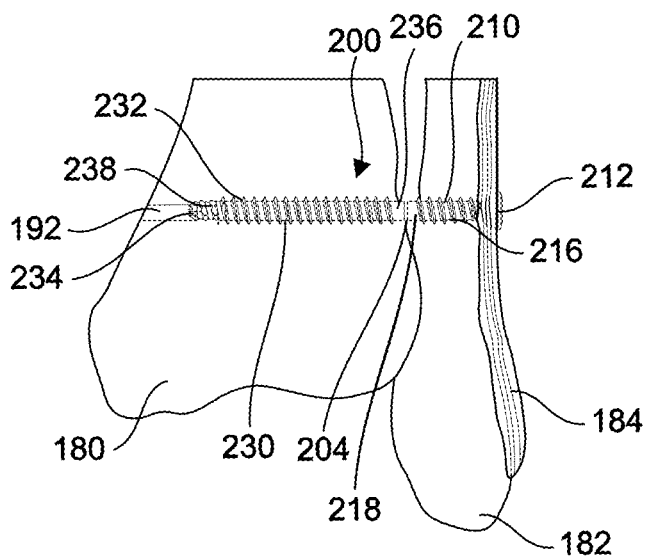
FIG. 19 is a posterior view of the tibia and fibula of FIG. 18 with the implant of FIG. 13 inserted through a plate, fibula, and into the tibia, in accordance with an aspect of the present disclosure.

Referring now to FIGS. 8-10 and 17-19, a method of inserting the implant 200 is shown. The method may include forming the opening 192, as shown in FIGS. 8-10 and described in greater detail above with reference to implant 100, which will not be described again here for brevity sake. As shown, the opening 192 may be, for example, formed through an opening in a plate 184 positioned on the lateral aspect of the fibula 182. Alternatively, where a plate 184 is not necessary, the opening 192 may be formed through the bones 180, 182 without alignment with a plate 184. Next, as shown in FIG. 17, the method may include inserting the implant 200 with a driver instrument 194 into the opening 192 in the bones 180, 182. The implant 200 may be inserted to position the anchor member 230 in the tibia 180, the head member 210 in the fibula 182, and the breakaway portion 204 in a tibiofibular space or gap, as shown in FIG. 18. The space or gap d may be, for example, approximately 3 mm. Once the implant 200 is in the desired position, the driver instrument 194 may be removed from the head member 210 of the implant 200, as shown in FIGS. 18 and 19. Finally, the surgical procedure may be completed.

Immediately after surgery, the joint is supported by the rigid fixation of the implant 200. Once sufficient healing has occurred to permit weight bearing on the limb of the patient, the implant 200 will break at the breakaway portion 204. After the breakaway portion 204 fractures or breaks, physiologic motion between the tibia 180 and fibula 182 is restored and the implant 200 may remain in place. If the implant 200 does need to be removed, the drive feature 238 positioned on the second end of the anchor member 230 may be used to remove the anchor member 230 and the tool engagement opening 214 positioned on the first end of the head member 210 may be used to remove the head member 210.

FIGS. 20-23 illustrates another exemplary alternative implant 300. The exemplary implant 300 of FIGS. 20-23 is substantially similar to the exemplary implant 100 of FIGS. 1-12 and/or the exemplary implant 200 of FIGS. 13-19, and therefore like reference numerals preceded by the numeral "3," as opposed to "1" or "2," are used to indicate like elements, aspects, functions, actions, configurations and the like. The implant 300 of FIGS. 20-23 may include any of the elements, aspects, functions, actions, configurations and the like of the implant 100 of FIGS. 1-12 and/or the implant 200 of FIGS. 13-19. The description above directed thereto with respect to the implant 100 of FIGS. 1-12 and/or the implant 200 of FIGS. 13-19 thereby equally applies to the exemplary implant 300 of FIGS. 20-23, including description regarding alternative embodiments thereto (i.e., modifications, variations or the like).

Figure 20:
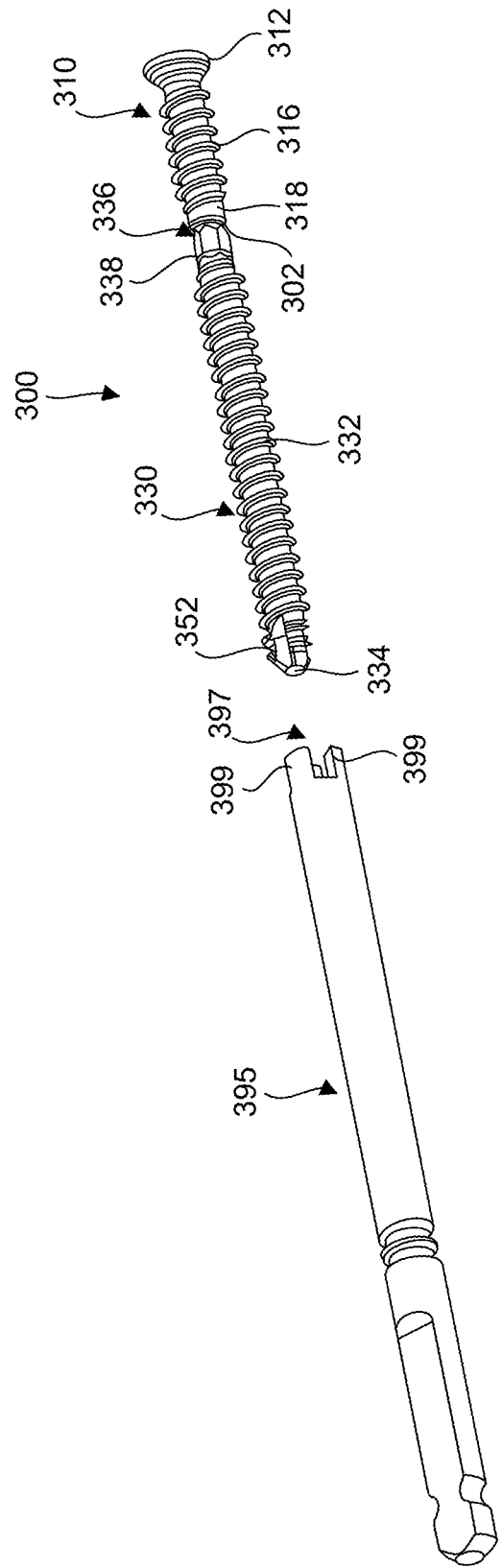
FIG. 20 is a side perspective view of one embodiment of an implant and removal instrument, in accordance with an aspect of the present disclosure.
Figure 21:
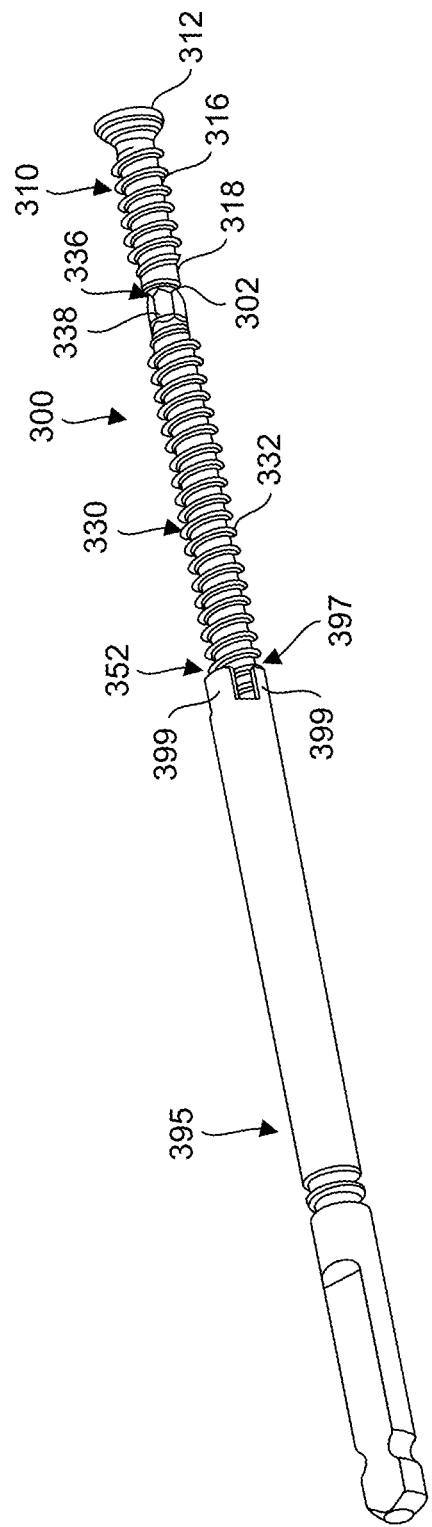
FIG. 21 is a side perspective view of the implant and removal instrument of FIG. 20 in an engaged state, in accordance with an aspect of the present disclosure.
Figure 22:
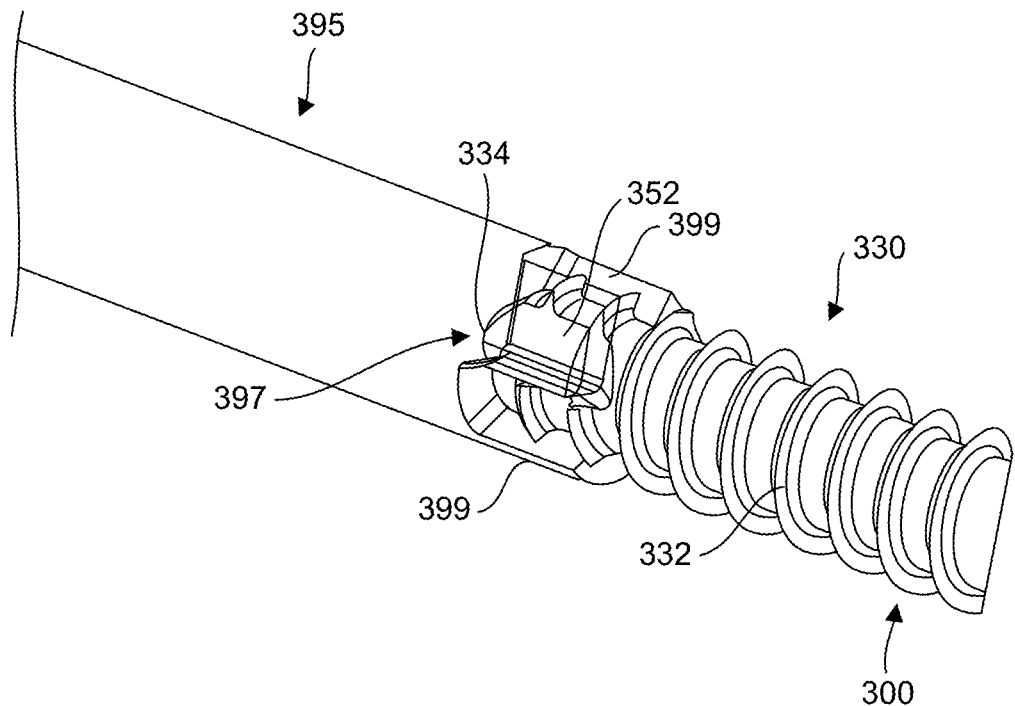
FIG. 22 is a side enlarged perspective view of a portion of the implant and removal instrument of FIG. 20 in an engaged state, in accordance with an aspect of the present disclosure.

As shown in FIGS. 20 and 22, the shaft distal end 334 at the second end of the implant 300 and the shaft portion 332 of the anchor member 330 may be relatively blunt or bullet-shaped. For example, the shaft distal end 334 may include a flat or planar distal surface oriented normal to the longitudinal axis and/or axis of rotation of the implant 300. As shown in FIGS. 20-23, the anchor member 330 of the implant 300 may also include a distal feature or portion 352 positioned at the distal or second end 334 of the anchor member 330 adjacent to, or extending from, the distal end 334. The distal portion 352 may comprise a plurality of circumferentially spaced or arranged longitudinally extending flutes, indentations or grooves. For example, as shown in FIGS. 20-23, the distal feature or portion 352 may comprise three (3) circumferentially spaced or arranged longitudinally extending flutes, indentations or grooves.

The distal feature or portion 352 may be configured to engage, mate or cooperate with an extraction instrument 395, as shown in FIGS. 20-23. In some embodiments, the extraction instrument 395 may be a medial extraction instrument. As shown in FIGS. 20-23, the extraction instrument 395 may include an internal aperture or cavity 397 extending into a free end thereof. The end of the extraction instrument 395 may also include a plurality of circumferentially spaced or arranged longitudinally extending projections, fingers or teeth 399, as shown in FIGS. 20-23. Gaps or spaces may circumferentially extend between adjacent projections 399 that are configured to accommodate the portions of the anchor member 330 that are void of the distal feature/grooves 352. The number and configuration of the plurality of circumferentially arranged longitudinally extending projections 399 may correspond to the circumferentially arranged longitudinally extending grooves of the distal feature or portion 352.

Figure 23:
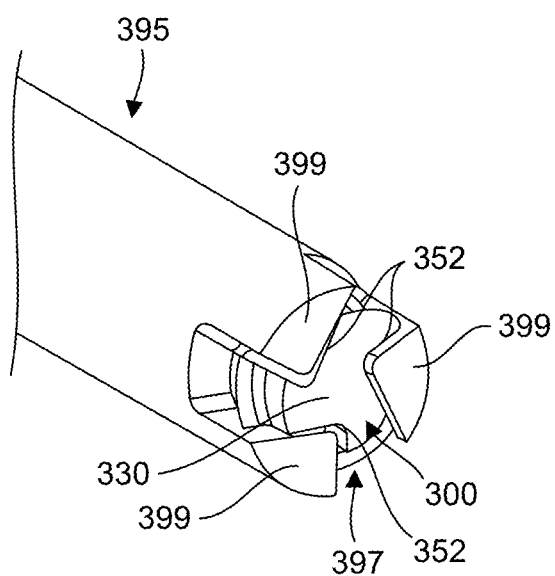
FIG. 23 is a side enlarged perspective cross-sectional view of a portion of the implant and removal instrument of FIG. 20 in an engaged state, in accordance with an aspect of the present disclosure.

A shown in FIGS. 21-23, the plurality of circumferentially arranged longitudinally extending projections 399 may be configured to engage (e.g., mate or otherwise extend within) the plurality of circumferentially spaced or arranged longitudinally extending grooves of the distal portion 352. Specifically, the end of the extraction instrument 395 may engage over the distal end 334 and distal portion 352 of the implant 300 such that the distal end 334 (and potentially the distal portion 352) is positioned within the internal cavity 397 with the plurality of circumferentially arranged longitudinally extending projections 399 engaged or mated within the plurality of circumferentially arranged longitudinally extending grooves of the distal portion 352, as shown in FIGS. 21-23. The extraction instrument 395 and the implant 300 may thereby be rotationally fixed or coupled together. In this way, the extraction instrument 395 may extend to the distal end 334 of the implant 300 and engage the distal portion 352, and apply a torque thereto to axially or longitudally drive the implant, potentially after implantation. The extraction instrument 395 may thereby be utilized to remove the implant after implantation.

As may be recognized by those of ordinary skill in the art based on the teachings herein, numerous changes and modifications may be made to the above-described and other embodiments of the present invention without departing from the scope of the invention. The head member, anchor member, breakaway portion, and other components of the implant and/or system as disclosed in the specification, including the accompanying abstract and drawings, may be replaced by alternative component(s) or feature(s), such as those disclosed in another embodiment, which serve the same, equivalent or similar purpose as known by those skilled in the art to achieve the same, equivalent or similar results by such alternative component(s) or feature(s) to provide a similar function for the intended purpose. In addition, the implants and systems may include more or fewer components or features than the embodiments as described and illustrated herein. For example, the components and features of FIGS. 1-4, 11 and 12, FIG. 5, FIG. 6, FIG. 7, FIGS. 13-19 and FIGS. 20-23 may all be used interchangeably and in alternative combinations as would be modified or altered by one of skill in the art. Accordingly, this detailed description of the currently-preferred embodiments is to be taken in an illustrative, as opposed to limiting of the invention.

The terminology used herein is for the purpose of describing particular embodiments only and is not intended to be limiting of the invention. As used herein, the singular forms "a", "an" and "the" are intended to include the plural forms as well, unless the context clearly indicates otherwise. It will be further understood that the terms "comprise" (and any form of comprise, such as "comprises" and "comprising"), "have" (and any form of have, such as "has", and "having"), "include" (and any form of include, such as "includes" and "including"), and "contain" (and any form of contain, such as "contains" and "containing") are open-ended linking verbs. As a result, a method or device that "comprises,"

"has," "includes," or "contains" one or more steps or elements possesses those one or more steps or elements, but is not limited to possessing only those one or more steps or elements. Likewise, a step of a method or an element of a device that "comprises," "has," "includes," or "contains" one or more features possesses those one or more features, but is not limited to possessing only those one or more features. Furthermore, a device or structure that is configured in a certain way is configured in at least that way, but may also be configured in ways that are not listed.

The invention has been described with reference to the preferred embodiments. It will be understood that the architectural and operational embodiments described herein are exemplary of a plurality of possible arrangements to provide the same general features, characteristics, and general system operation. Modifications and alterations will occur to others upon a reading and understanding of the preceding detailed description. It is intended that the invention be construed as including all such modifications and alterations.

What is claimed is:

1. An implant, comprising:
   a head member;
   a breakaway portion; and
   an anchor member coupled to the head member, the anchor member comprising:
      a shaft portion with a first and second end;
      a proximal coupling portion extending from the first end of the shaft portion of the anchor member to the breakaway portion and comprising an internal drive opening extending into a first end of the proximal coupling portion and toward a second end of the proximal coupling portion coupled to the first end of the shaft portion of the anchor member; and
      a distal portion extending from the second end of the shaft portion of the anchor member;
   wherein the head member is coupled to the anchor member by the breakaway portion.

2. The implant of claim 1, wherein the breakaway portion extends between a first end of the anchor member and a second end of the head member.

3. The implant of claim 2, wherein the breakaway portion comprises a circumferential groove that defines a first diameter that is less than a second diameter defined by a portion of the head member positioned proximate to the breakaway portion and a third diameter defined by a portion of the anchor member positioned proximate to the breakaway portion.

4. The implant of claim 3, wherein a ratio of the first diameter to the second and/or the first diameter to the third diameter is within a range of 64% to 89%.

5. The implant of claim 1, wherein the breakaway portion comprises a plurality of openings positioned around a circumference of the breakaway portion that extend in a radial direction from a center axis of the breakaway portion.

6. The implant of claim 1, wherein the breakaway portion comprises at least one through hole extending through a diameter of the breakaway portion.

7. The implant of claim 1, wherein the head member comprises:
   a shaft portion with a first end and a second end extending from the breakaway portion;
   a head portion extending from the first end of the shaft portion; and
   a tool engagement opening extending into the head portion toward the second end of the shaft portion.

8. The implant of claim 7, wherein a portion of the shaft portion comprises external threads, and wherein a portion of the shaft portion at the second end is void of external threads.

9. The implant of claim 1, wherein at least a portion of the shaft portion of the anchor member comprises external threads, and wherein the proximal coupling portion is void of external threads.

10. The implant of claim 1, wherein the proximal coupling portion comprises outer planar surfaces circumferentially arranged about the proximal coupling portion.

11. The implant of claim 1, wherein the distal portion comprises at least one cutting flute.

12. The implant of claim 1, wherein the distal portion comprises a plurality of circumferentially arranged longitudinally extending flutes.

13. The implant of claim 1, wherein the head member, the breakaway portion and the anchor member are integral.

14. The implant of claim 1, comprising a cannulated opening extending through an entire length of the implant extending from a proximal head portion of the head member defining a first end of the implant to a distal end of the anchor member defining a second end of the implant.

15. The implant of claim 1, wherein the breakaway portion is formed of a bio-resorbable material.

16. A method for inserting an implant, comprising:
   obtaining an implant, wherein the implant comprises:
      a head member;
      a breakaway portion; and
      an anchor member coupled to the head member, wherein the head member is coupled to the anchor member by the breakaway portion and comprises an internal drive opening extending into the anchor member adjacent the breakaway portion;
   engaging the head member of the implant with an insertion instrument; and
   inserting the implant into a patient such that the head member is positioned within a first bone, the anchor member is positioned within a second bone, and the breakaway portion is positioned at least partially within a gap extending between the first and second bones.

17. The method of claim 16, wherein the first bone is a fibula, the second bone is a tibia, and the gap is a tibiofibular space.

18. The method of claim 16, wherein the breakaway portion comprises a circumferential groove that defines a first diameter that is less than a second diameter defined by a portion of the head member positioned proximate to the breakaway portion and a third diameter defined by a portion of the anchor member positioned proximate to the breakaway portion, wherein a ratio of the first diameter to the second and/or the first diameter to the third diameter is within a range of 64% to 89%, and wherein the anchor member comprises a distal end portion comprising a plurality of circumferentially arranged longitudinally extending flutes.

19. The implant of claim 1, wherein the internal drive opening comprises a hexagonal or multi-lobed drive opening.

20. The implant of claim 1, wherein the breakaway portion comprises at least one channel extending into the implant from an exterior surface thereof.

* * * * *